United States Patent [19]

Liverani

[11] Patent Number: 4,930,520

[45] Date of Patent: Jun. 5, 1990

[54] EARPIECE FOR AUDITORY TESTING OF INFANTS

[75] Inventor: Maurizio Liverani, Stanford, Calif.

[73] Assignee: Algotek, Inc., Redwood city, Calif.

[21] Appl. No.: 735,423

[22] Filed: May 16, 1985

[51] Int. Cl.⁵ .............................................. A61B 5/12
[52] U.S. Cl. .................................. 128/746; 128/866; 128/867
[58] Field of Search ..................... 128/746, 639–640, 128/644, 151–152, 864–868

[56] References Cited

U.S. PATENT DOCUMENTS

| | | | |
|---|---|---|---|
| 2,802,214 | 8/1957 | Hanks | 128/152 |
| 3,841,325 | 10/1974 | Pickard | 128/151 |
| 3,938,614 | 2/1976 | Ahs | 128/151 X |
| 3,944,018 | 3/1976 | Satory | 128/151 X |
| 4,009,707 | 3/1977 | Ward | 128/746 |
| 4,024,499 | 5/1977 | Bosscher | 128/746 X |
| 4,036,235 | 7/1977 | Hathaway | 128/151 X |
| 4,134,153 | 1/1979 | Voorhees | 128/151 X |
| 4,344,425 | 8/1982 | Strauss | 128/152 |
| 4,375,744 | 6/1981 | Thornton | 128/731 |
| 4,408,605 | 10/1983 | Doehrr et al. | 128/151 X |
| 4,437,538 | 3/1984 | Ohlsson et al. | 128/152 X |

FOREIGN PATENT DOCUMENTS 2010640  6/1979  United Kingdom ............... 128/746

*Primary Examiner*—Angela D. Sykes
*Attorney, Agent, or Firm*—Townsend and Townsend

[57] ABSTRACT

An earpiece is provided for use in auditory testing of infants which is formed of a toroidal baffle of anechoic insulative foam material having on one side a clear window and on the opposing side an adhesive material for binding to the region around the ear of an infant. The earpiece is further provided with a pneumatic connector for coupling acoustic energy through a pneumatic tube into the cavity formed around the ear of a subject when the earpiece is attached.

16 Claims, 1 Drawing Sheet

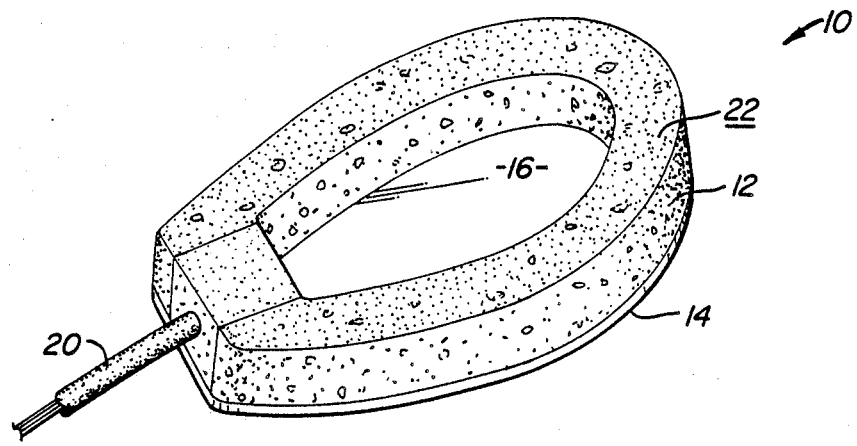
FIG._1.
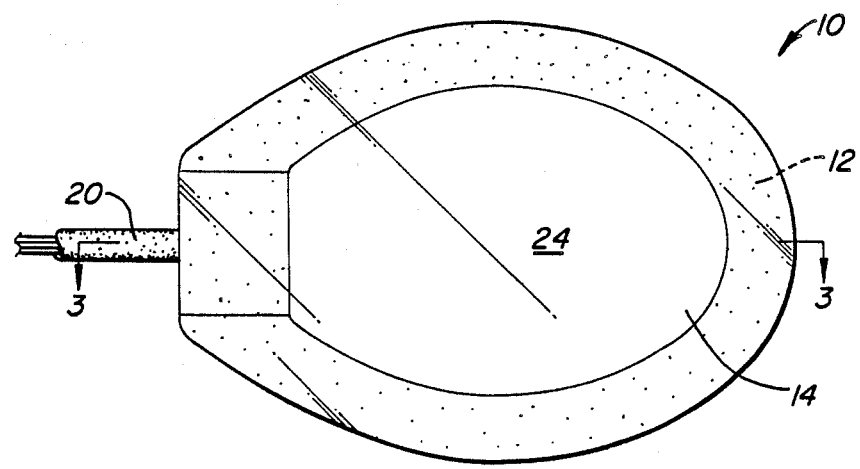
FIG._2.
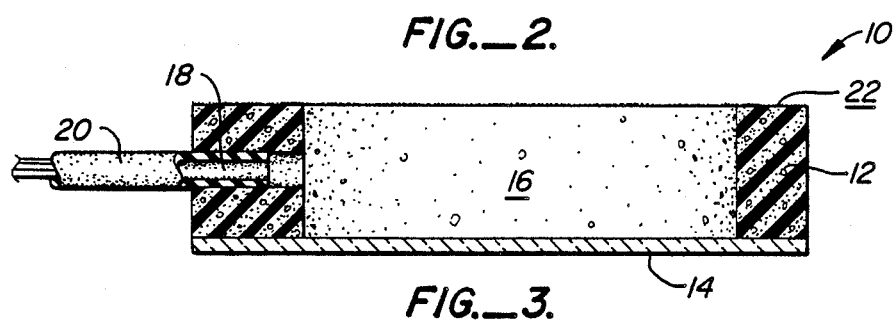
FIG._3.

4,930,520

EARPIECE FOR AUDITORY TESTING OF INFANTS

BACKGROUND OF THE INVENTION

This invention relates to infant hearing screening, and particularly to an earpiece for use in connection with equipment for stimulating the reaction to sound in an infant such as a premature infant.

There is a need for a hearing screener to identify handicapping hearing loss in newborn infants. Prototype auditory response devices have been developed as for example as described in U.S. Pat. No. 4,275,744 issued in the name of Thornton and Obenour. The disclosure of U.S. Pat. No. 4,275,744 is incorporated herein and made a part hereof. In summary, the '744 patent describes a technique whereby audible signals stimulate changes in electro-encephalographic signals stimulate changes in electro-encephalographic signals of a person. The measured brain activity allows diagnosis of certain types of hearing impairment.

If a hearing impairment is sufficiently early, therapy can be undertaken to minimize the potential effects of handicapping hearing loss, such as would otherwise lead to speech and language handicaps.

One of the needs in connection with the hearing screening device of the type described in Thornton is a useful and effective acoustic coupling device. Heretofore, the conventional coupling device has been an earphone type transducer designated TDH39 or TDH49. Such a transducer is bulky and heavy, which made it particularly undesirable when used in connection with premature infants. Another alternative has been the provision of a testing facility including a sound proof room. Neither alternative has been particularly attractive in practical applications. Accordingly, there is a need to provide a better acoustic coupler for a hearing screener.

SUMMARY OF THE INVENTION

According to the invention, an earpiece is provided for use in auditory testing of infants which is formed of a toroidal baffle of anechoic insulative foam material having on one side a clear window and on the opposing side an adhesive material for binding to th region around the ear of an infant. The earpiece is further provided with a pneumatic connector for coupling acoustic energy through a pneumatic tube into the cavity formed around the ear of a subject when the earpiece is attached.

The earpiece, according to the invention, is lightweight, pliant and comfortable so that it does not interfere with reasonable activity of the infant, the inventive earpiece also minimizes the need for sound proofing of the testing facilities. The earpiece may be used with electrical to acoustic transducers remote from the earpiece.

The invention will be better understood by reference to the following detailed description in connection with the accompanying drawings.

BRIEF DESCRIPTION OF THE DRAWINGS

FIG. 1 is a perspective view of an earpiece in accordance with the invention.

FIG. 2 is a top plan view of the earpiece according to the invention.

FIG. 3 is a side cross-sectional along line 3—3 of FIG. 2.

DESCRIPTION OF SPECIFIC EMBODIMENTS

Referring to FIG. 1, there is shown an earpiece 10 in accordance with the invention. The earpiece 10 comprises a toroidal baffle 12 and a backing plate 14. The backing plate 14 and baffle 12 form a cavity 16 of generally the size and depth necessary to accommodate the ear of an infant when the baffle 12 surrounds the external ear.

Referring also to FIGS. 2 and 3, the baffle 12 has provided therein a passage 18 for insertion of a tube 20. The tube 20 is an air tube for carrying acoustic energy to and from the cavity 16. The tube may be removable, and the earpiece 10 may be disposable.

An adhesive layer 22 is provided around the margin of the baffle opposing the backing plate 14. The adhesive is preferably a light, non-toxic, non-irritative and waterproof material which is used for binding the surface of the baffle 12 with the skin around the external ear of an infant.

Referring to FIG. 2, the backing plate 14 is preferably of transparent material such as clear plastic so as to form a window 24 through which the external ear may be observed. A window 24 is an important advantage because it allows easy alignment of the earpiece 10 with respect to the external ear. By contrast, prior electronic ear pieces had no window, and generally incorporated an electronic element in the earpiece.

The baffle 12 is generally formed of a porous, acoustically absorbant pliant elastomeric material such as high density rubber foam. One such material is sold under the brand name "Poron". Specifically, the material is vinyl nitril foam approximately one-half inch thick.

An important advantage of this type earpiece is that it is disposable. Since it is disposable, it is relatively easy to provide a sterile device packaged for a single use to be discarded thereafter. Thus, the earpiece 10 can be eliminated as a source of contamination and potential infection in a newborn.

In addition, because the foam is pliant and is provided with an adhesive coating, it can be formed to conform to the contour of the side of the head, thereby to exclude, or at least to minimize, sound leakage into the cavity 16. It should be understood that the sound leakage through the window 24 and the baffle 12 is still expected. However, the earpiece 10 is designed for use with noise canceling equipment which monitors background sound level within the cavity, thereby to minimize the effect of sound leakage.

Another principal advantage of an earpiece according to the invention is its extreme lightness as compared to other ear pieces. This lightness is important for an infant because it is extremely sensitive to weight and bulkiness of the earpiece. An uncomfortable earpiece can affect brain output and adversely affect a diagnosis of hearing problems by interfering with the normal brain wave patterns in response to acoustic sound. It is the intention of the hearing tests to stimulate brainwave action only in response to acoustic energy, and not to any other cause.

The invention has now been explained with reference to specific embodiments. Other embodiments will be apparent to those of ordinary skill in the art in view of the present disclosure. For example, other configurations of baffle and window arrangements may well be within contemplation of the invention. It is therefore not intended that this invention be limited except as indicated by the appended claims.

I claim:

1. An earpiece for use in testing the hearing of an infant comprising:
   a baffle forming a toroid shaped to encircle an ear of an infant and to conform to the side of an infant head;
   a flat backing plate attached to and forming an enclosure on one side of the baffle for defining a cavity; and
   means for forming a passage into the cavity formed by said baffle and said backing plate for conveying acoustic energy to and from the cavity.

2. An apparatus according to claim 1 further comprising an adhesive means upon the side of said baffle opposing said backing plate for bonding with the side of an infant head.

3. The apparatus according to claim 2 wherein said baffle is formed of a pliant acoustically absorbent foam elastomeric material so that said baffle can be adapted to conform to the contour of a head of an infant around an external ear of said infant.

4. The apparatus according to claim 1 wherein said backing plate is transparent for forming a window for viewing the infant ear.

5. The apparatus according to claim 1 wherein said baffle is formed of a pliant acoustically absorbent foam elastomeric material so that said baffle can be adapted to conform to the contour of a head of an infant around an external ear of said infant.

6. The apparatus according to claim 1 wherein said backing plate is transparent for forming a window for viewing the infant ear.

7. An apparatus for use in testing the hearing of an infant comprising:
   an earpiece, said earpiece comprising a toroidal baffle shaped to encircle an ear of an infant and to conform to the side of an infant head, the toroidal baffle being formed of a pliant acoustically absorbent elastomeric foam material, and means for enclosing one side of said baffle to form a cavity of a size for surrounding an external ear of an infant, said cavity forming means being transparent for forming a window for viewing the infant ear; and
   means for conveying sound to and from said cavity.

8. The apparatus according to claim 7 further including adhesive means, said adhesive means being applied to said baffle opposing said viewing means for bonding with the side of the infant head.

9. An earpiece for use in testing the hearing of an infant comprising:
   a baffle forming a toroid shaped to encircle an ear of an infant and to conform to the side of an infant head; and
   a flat transparent panel attached to and enclosing one side of the baffle defining a cavity having a window for viewing the infant ear.

10. The apparatus according to claim 9 further comprising an adhesive means upon the side of said baffle opposing said transparent panel for bonding with the side of the infant head.

11. The apparatus according to claim 10 wherein said baffle is formed of a pliant acoustically absorbent foam elastomeric material so that said baffle can be adapted to conform to the contour of a head of an infant around an external ear of said infant.

12. The apparatus according to claim 11 further comprising means for forming a passage through the baffle and into the cavity formed by said baffle and said transparent panel for conveying acoustic energy to and from the cavity.

13. The apparatus according to claim 9 wherein said baffle is formed of a pliant acoustically absorbent foam elastomeric material so that said baffle can be adapted to conform to the contour of a head of an infant around an external ear of said infant.

14. The apparatus according to claim 9 further comprising means for forming a passage through the baffle and into the cavity formed by said baffle and said transparent panel for conveying acoustic energy to and from the cavity.

15. An earpiece for use in testing the hearing of an infant comprising:
   a baffle forming a toroid shaped to encircle an ear of an infant and to conform to the side of an infant head, the baffle being formed of a pliant acoustically absorbent foam elastomeric material;
   a rigid flat transparent panel attached to and forming an enclosure on one side of the baffle defining a cavity having a window for viewing the infant ear;
   adhesive means upon the side of the toroidal baffle opposing the transparent panel for bonding with the side of the infant head; and
   an aperture through the toroidal baffle for connecting the baffle to a pneumatic tube for conveying acoustic energy to and from the cavity.

16. A method for testing the hearing of an infant comprising the steps of:
   forming an earphone for enclosing the ear of an infant by attaching a flat transparent panel to one side of a pliant elastomeric acoustically absorbent foam toroidal baffle, the baffle being shaped to encircle an ear of an infant and to conform to the side of an infant head;
   bonding the earpiece with the side of the infant head, while viewing the infant ear;
   conveying acoustic energy into the earpiece while the earpiece is bonded with the infant head for testing the hearing of the infant.

* * * * *